Figure 1:
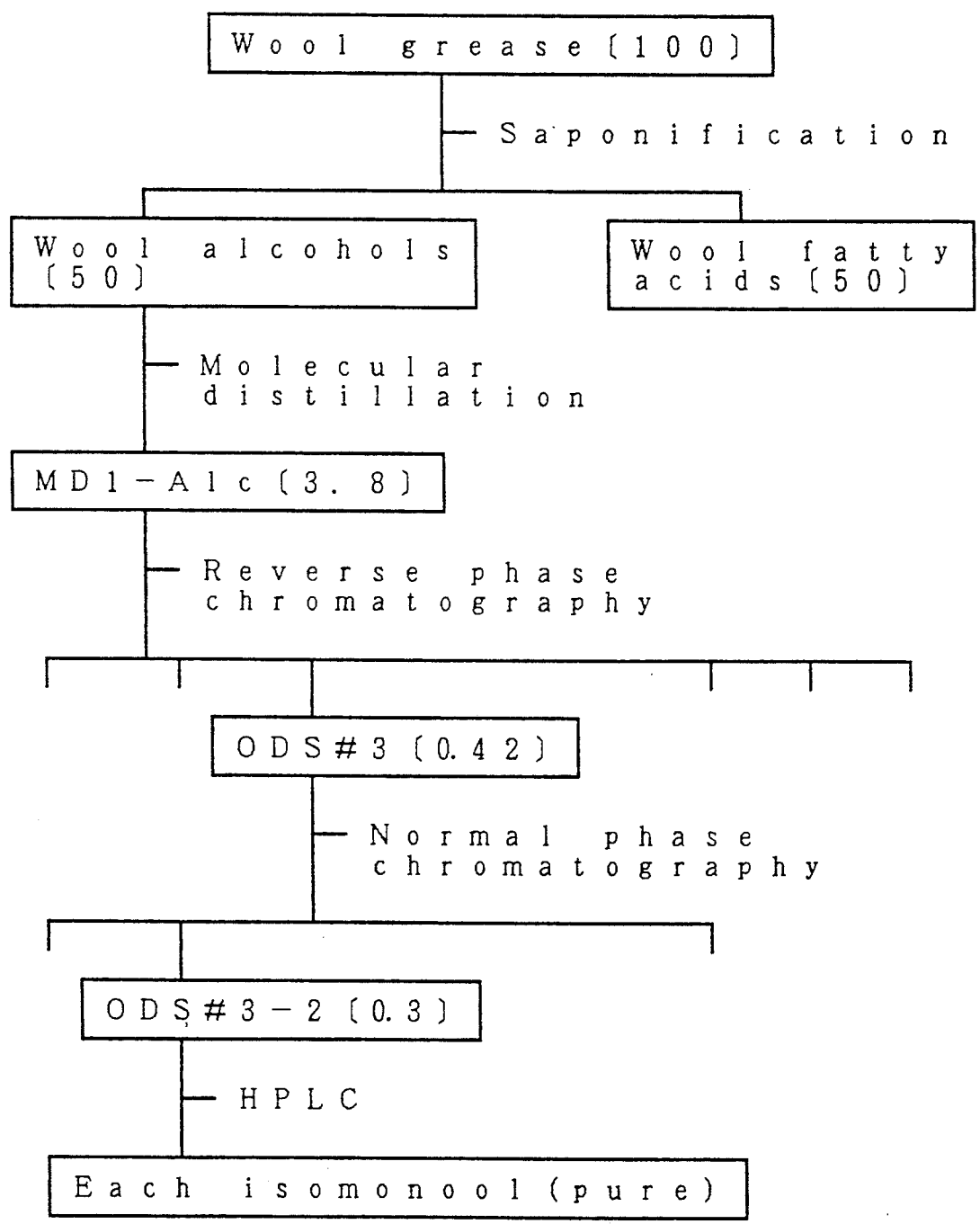

United States Patent [19]

Nakamura et al.

[11] Patent Number: 5,162,304
[45] Date of Patent: Nov. 10, 1992

[54] PHARMACEUTICAL COMPOSITIONS AND METHODS FOR TREATMENT AND PROPHYLAXIS OF CANCER

[75] Inventors: Shingo Nakamura, Joyo; Yoshichika Nishimura, Kyoto; Nobuhiko Miwa, 20-17 Mikkaichimachi, Shobara-shi, Hiroshima-ken, all of Japan

[73] Assignees: Dai-Ichi Kogyo Seiyaku Co., Ltd., Kyoto; Nobuhiko Miwa, Hiroshima, both of Japan

[21] Appl. No.: 686,975

[22] Filed: Apr. 18, 1991

[30] Foreign Application Priority Data

Apr. 19, 1990 [JP] Japan .................. 2-103914
Apr. 19, 1990 [JP] Japan .................. 2-103915

[51] Int. Cl.$^5$ ............ A61K 37/10; A61K 31/045
[52] U.S. Cl. ................................. 514/8; 514/724
[58] Field of Search ........................ 514/724, 8

[56] References Cited

U.S. PATENT DOCUMENTS 4,985,466 1/1991 Deguchi .................. 514/724

Primary Examiner—Frederick E. Waddell
Assistant Examiner—Raymond J. Henley, III
Attorney, Agent, or Firm—Millen, White, Zelano and Branigan

[57] ABSTRACT

A pharmaceutical composition comprising, in admixture with a pharmacologically acceptable carrier, an isomonool of the formula $$\overset{R}{\underset{|}{CH_3CH(CH_2)_nCH_2OH}}$$

wherein R is an alkyl group with 1 to 5 carbon atoms, and n is an integer of 4 to 22, have carcinostatic, carcinostasis-reinforcing and carcinogenesis-preventing activity.

8 Claims, 7 Drawing Sheets

PHARMACEUTICAL COMPOSITIONS AND METHODS FOR TREATMENT AND PROPHYLAXIS OF CANCER

BACKGROUND OF THE INVENTION

This invention relates to novel pharmaceutical compositions and methods for treatment and prophylaxis of cancer, more specifically for carcinostasis, reinforcement of carcinostasis and prevention of carcinogenesis.

Up to now, several types of carcinostatic agents have been known. These include: alkylating agents which exhibit the carcinostatic activity by alkylating such biopolymers with indispensable roles as nucleic acids and enzymes, metabolic antagonists which inhibit metabolism of nucleic acids, mitotic poisons which affect biosynthesis of nucleic acids in the cell, carcinostatic antibiotics which exhibit cytocidal activity against the cells in rapid proliferation, carcinostatic compounds of plant origin, and hormones.

On the other hand, amphotericin B and the like have been investigated as carcinostasis-reinforcing agents which may exhibit effects on improvement in absorption of drugs with poor absorbability to cancer cells and thus enhance carcinostatic effects of carcinostatic agents such as bleomycin and adriamycin. However none of them have come to attain any notable effect.

Any of carcinostatic agents known from the prior art do not get rid of causing side effects, and few of them exhibit a satisfactory effect. Consequently, carcinostatic agents with improved characteristics have been needed. And there also have been needs for excellent carcinostasis-reinforcing agents in order to let carcinostatic agents express their full effects.

Meanwhile, there is a leading hypothesis that carcinogenesis may be triggered through two steps mediated by an initiator and a promoter. However, the mechanisms of carcinogenesis is not known in relation to their influences exerted upon human body in daily life. Thus, prevention of carcinogenesis can only be pursued by a trial-and-error method based on experiences. Consequently, the development of carcinogenesis-preventing agents has been far behind that of anti-cancer agents.

The criteria for carcinogenesis-preventing agents may be as follows.

First, carcinogenesis-preventing agents, in general, are required to possess greater safety than that required for anti-cancer agents, and they have to be totally free of side effects.

Secondly, they are required to be effective by oral administration so as to be administered easily in daily life.

Thirdly, they are required not only to be effective on particular experimental cancers but also to have a wide spectrum against various types of cancers which have actually the higher rate of incidence.

On the basis of aforementioned situation, the inventors have screened substances of sebum origin in order to find compounds which will be useful as agents for treatment and prophylaxis of cancer, assuming that the development of such agents should be started from the naturally and physiologically occurring "bio-substances" in the body of higher animals. As the result, some compounds that fulfill the aforementioned requirements were discovered.

These compounds have both carcinostatic and carcinostasis-reinforcing effects.

Moreover, they are thought to be useful for general prevention of carcinogenesis, for prevention of recurrence after completion of cancer treatment, for prophylaxis of occupational cancer and for prophylaxis in those who are hereditarily liable to certain cancers. Since the compounds of the present invention are chemically stable and can remain unchanged after cooking, they may be used as food additives and for functional foods or health foods. The compounds of the present invention are compounds which occur naturally in sebum, and they may, accordingly, be readily accepted by general people.

SUMMARY OF THE INVENTION

Through an intensive investigation for a carcinostatic, carcinostasis-reinforcing or carcinogenesis-preventing agent which would cause no side effects, the present inventors have discovered that isomonools represented by the general formula:

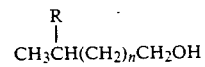

wherein R is an alkyl group with 1 to 5 carbon atoms, and n is an integer of 4 to 22, are excellent in such activities.

Thus, the present invention provides carcinostatic, carcinostasis-reinforcing and carcinogenesis-preventing compositions containing as an active ingredient an isomonool represented by the general formula (I):

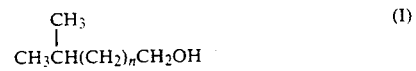

wherein R is an alkyl group with 1 to 5 carbon atoms, and n is an integer of 4 to 22.

DETAILED DISCUSSION

In the present invention, the length of the alkyl chain of the isomonools in the general formula (I) is defined by n which is an integer of 4 to 22 and R which is an alkyl group with 1 to 5 carbon atoms. When n is less than 4, none of carcinostatic, carcinostasis-reinforcing and carcinogenesis-preventing activities are exhibited. Likewise, when n is greater than 22, none of such activities are exhibited. When R is an alkyl group with 6 or more carbon atoms, none of such activities are exhibited, either. A marked increase in potency in activities is observed when n is 10 to 16, and when R is methyl or ethyl in the general formula (I). Among others, 14-methyl-1-pentadecanol of the formula (II):

and 14-methyl-1-hexadecanol of the formula (III):

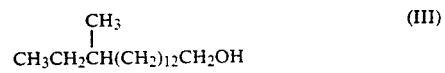

are especially potent in activities and, therefore, particularly preferred.

The isomonools utilized in the present invention may be produced by decomposing naturally occurring compounds such as waxes. Examples of such naturally occurring compounds include wool wax, spermaceti, beewax, white wax and carnauba wax.

The isomonools utilized in the present invention may be obtained, for example, as follows (FIG. 1, a flowchart of the production process).

SAPONIFICATION

A naturally occurring compound such as wool grease is suspended in water in the presence of 1.18 times of an alkali (NaOH) on molar basis, and saponification reaction is conducted for 3 hours while stirring at $135° \pm 5°$ C. under pressure in an autoclave.

SEPARATION OF ALCOHOLS FROM FATTY ACIDS

To the resulting saponification product (the mixture of sodium salts of higher fatty acids and higher alcohols) are added water and methylethylketone (hereinafter referred to as MEK). The mixture is transferred into a separating funnel and heated to 70° to 75° C. to extract alcohols into MEK. The resulting solution of wool alcohols in MEK is evaporated in vacuo to give wool alcohols as a solid matter.

MOLECULAR DISTILLATION OF WOOL ALCOHOLS

The solid wool alcohols thus obtained is subjected to molecular distillation to obtain a fraction with a lower boiling point (temperature; <80° C., pressure; $1 \times 10^{-2}$ Torr). The fraction is hereinafter referred to as MD1-Alc.

FRACTIONATION OF MD1-ALC BY REVERSE PHASE COLUMN CHROMATOGRAPHY

MD1-Alc is separated into 6 fractions by reverse phase column chromatography (open column).

FRACTIONATING CONDITIONS

Solid phase: crushed ODS, pore size 60 Å, particle size 60/200 mesh (commercial name; YMC.GEL, YAMAMURA KAGAKU KENKYUSHO K.K.)
Eluant: $CHCl_3/CH_3OH/H_2O = 5/15/1$ (in volume).

The third fraction, which has the third highest polarity, is hereinafter referred to as ODS#3.

FRACTIONATION OF ODS#3 BY NORMAL PHASE COLUMN CHROMATOGRAPHY

ODS#3 is fractionated by normal phase column chromatography (open column).

FRACTIONATING CONDITIONS

Solid phase: silica gel, pore size 60 Å, TYPE 60 Å SPECIAL, particle size 100/200 mesh (commercial name; SILICAR (trademark): produced by Mallinckrodt, distributed by DAIICHI KAGAKU YAKUHIN K.K.)
Eluants:
Eluant I, $CHCl_3/CH_3COCH_3 = 96/4$ (in volume)
Eluant II, $CH_3OH$.

The first and the second fractions are eluted with the eluant I, and the third with the eluant II. The second eluted fraction is hereinafter referred to as ODS#3-2.

FRACTIONATION OF ODS#3-2 BY HPLC

Separation and isolation of isomonools

ODS#3-2 is fractionated by HPLC to isolate the aimed compounds.

HPLC CONDITIONS

Column: TSK gel ODS-120T (commercial name, TOSO K.K.), 21.5 mm ID $\times$ 300 mm
Mobile phase: $CH_3OH/H_2O = 95/5$ (in volume)
Flow rate: 5.0 ml/min
Column temperature: room temperature.

The isomonools may be separated and isolated also by other methods. Examples of such other methods include the methods described by SATOSHI TAKANO, MAKOTO YAMANAKA, KIKUHIKO OKAMOTO and FUMIO SAITO (Allergens of lanolin: parts I and II, Part I: ISOLATION AND IDENTIFICATION OF THE ALLERGENS OF HYDROGENATED LANOLIN, JOURNAL OF THE SOCIETY OF COSMETIC CHEMISTS, 34, P 99-116 (1983)).

Examples of isomonools include iso—$C_{14}$—OH [12-methyl-1-tridecanol], iso—$C_{15}$—OH [13-methyl-1-tetradecanol], iso—$C_{16}$—OH [14-methyl-1-pentadecanol], iso—$C_{17}$—OH [15-methyl-1-hexadecanol] and iso—$C_{18}$—OH [16-methyl-1-heptadecanol] when R is methyl, and iso—$C_{15}$—OH [12-methyl-1-tetradecanol], iso—$C_{16}$—OH [13-methyl-1-pentadecanol], iso—$C_{17}$—OH [14-methyl-1-hexadecanol], iso—$C_{18}$—OH [15-methyl-1-heptadecanol] and iso—$C_{19}$—OH [16-methyl-1-octadecanol] when R is ethyl.

These isomonools may be used alone or in mixture with one or more other isomonools.

For preparing a composition of the present invention into the forms of injection or instillation, the isomonools may be admixed with a surfactant such as Pluronic F-68 (commercial name of a poloxamer, ASAHI DENKA K.K.), HCO-60 (commercial name, NIKKO CHEMICALS K.K.) and the like, and then dispersed with the aid of ultrasonic waves, or the isomonools may be processed into a type of composition such as a liposome suspension or an oil-in-water emulsion.

Such compositions may contain preservatives such as methyl p-hydroxybenzoate, stabilizers such as lecithin or linoleic acid, non-aqueous vehicles such as coconut oil and agents for suspension aid such as glucose.

For preparing composition for oral administration, the isomonools may be made into the form of capsules suitable for intestinal absorption by incorporating, for example, binders such as gelatin, stabilizers such as magnesium stearate, diluent bases such as lactose and disintegrators such as potato starch and by coating the capsules with acetylphthalylcellulose or methyl acrylate/methacrylate copolymer to form an enteric coating layer.

The isomonools may also be made into the forms of granules, sustained-release capsules for implant, a suppository, a nebulizer or a buccal preparation.

For use as a carcinostatic composition or a carcinogenesis-preventing composition, the dose (per 1 kg body weight per day for adult human) of the active ingredient may be preferably 5 to 1200 mg, particularly preferably 20 to 300 mg for parenteral preparations such as for intravenous or subcutaneous injection or instillation, and preferably 0.1 to 40 g, particularly preferably 0.5 to 8 g for oral preparations, for example, capsules.

For use as a carcinostasis-reinforcing composition, the dose may be preferably 0.45 to 102 mg, particularly preferably 1 to 28 mg for parenteral preparation, and preferably 0.005 to 5.2 g, particularly preferably 0.07 to 1.2 g for oral preparations.

The agents of the present invention are effective in treatment not only of ascites tumors and leukemia but also of solid tumors which include adenocarcinoma, squamous cell carcinoma, undifferentiated carcinoma and sarcoma in various tissues. The agents are effective not only in tumor-implanted animals but also on cultured malignant cells from human, mouse, rat, hamster and so on. It is thus indicated that the agents may have a direct lethal effect on tumor cells without specificity to animal species, and, therefore, they may be used as chemotherapeutic agents for cancer of human or domestic and other animals.

In addition, they are effective not only by direct application to the implanted tumor site but also by application to a remote site. As for toxicity, $LD_{50}$ is 5.1 to 17 g/kg for the rat by subcutaneous injection, and no side effects have been observed by repeated administration for 10 days at a dose of 1 to 2 g/kg.

The following is an example of the preparation methods of the isomonools, the active ingredients of the carcinostatic, carcinostasis-reinforcing and carcinogenesis-preventing compositions of the present invention. The scope of the present invention, however, is not limited by the example.

EXAMPLE 1

200 g of wool alcohol obtained by saponification of wool grease was subjected to molecular distillation to give 15.2 g of MD1-Alc as a fraction with a lower boiling point (temperature: $<80°$ C., pressure; $1 \times 10^{-2}$ Torr).

The MD1-Alc was separated into 6 fractions by reverse phase column chromatography (open column) using $CHCl_3/CH_3OH/H_2O = 5/15/1$ (in volume) mixture as an eluant. The third eluted fraction (ODS#3) was obtained in an amount of 1.68 g.

The ODS#3 was subjected to normal phase column chromatography (open column) and separated into 3 fractions using the eluants (the eluant I: $CHCl_3/CH_3COCH_3 = 96/4$ (in volume), the eluant II: $CH_3OH$).

The second eluted fraction (ODS#3-2) of the three was obtained in an amount of 0.96 g.

ODS#3-2 was fractionated by HPLC to isolate each of the aimed compounds.

Thus obtained were 14-methyl-1-pentadecanol, 14-methyl-1-hexadecanol, 16-methyl-1-heptadecanol, 16-methyl-1-octadecanol, 18-methyl-1-nonadecanol.

Capillary gas chromatography clearly demonstrated that each of these isomonools was isolated.

For determining chemical structures, $^{13}C$-NMR and GC-MS were applied, and these isolated compounds were identified to be the isomonools represented by the general formula (I) of the present invention.

Figure 2:
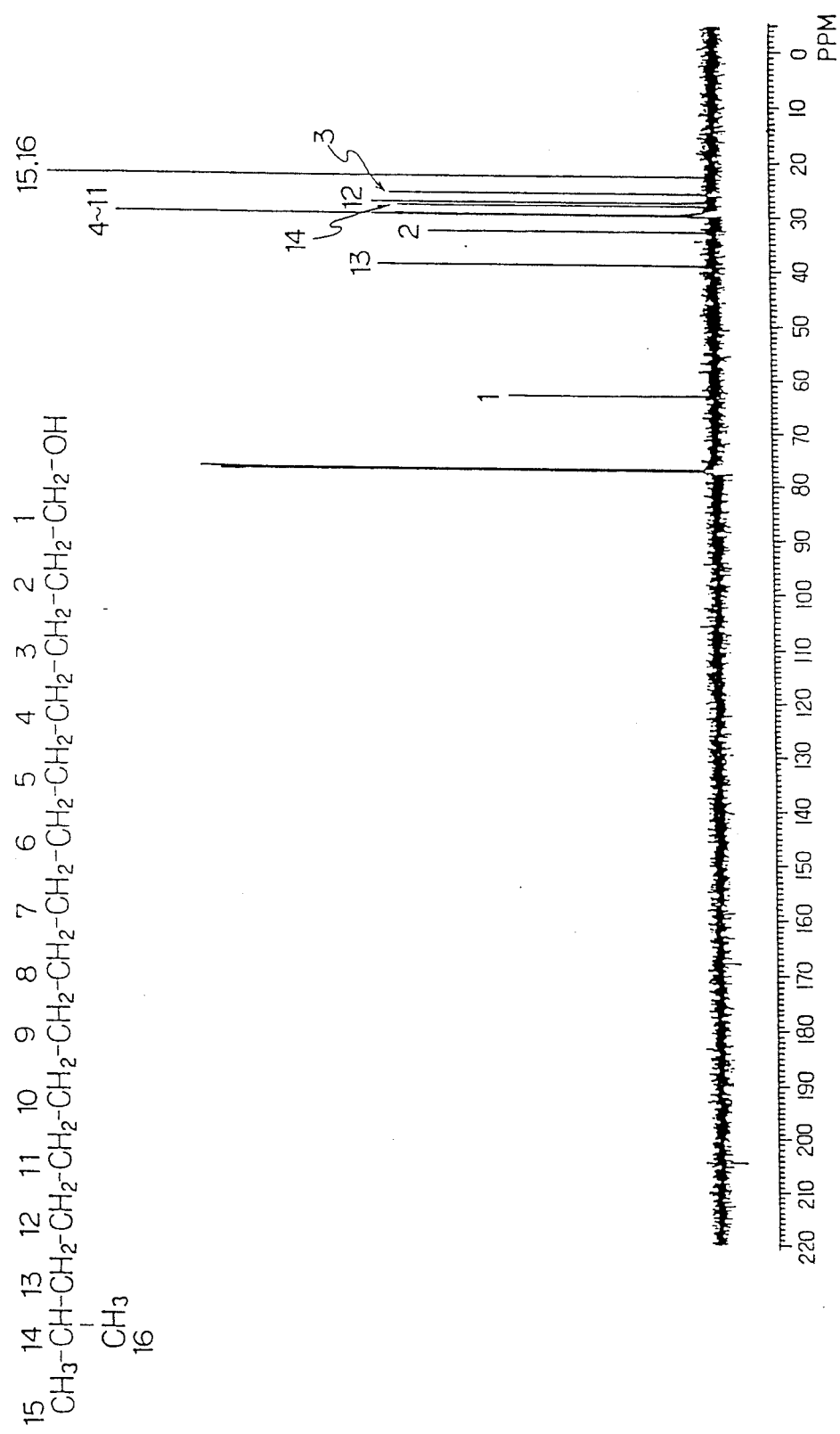
Figure 3:
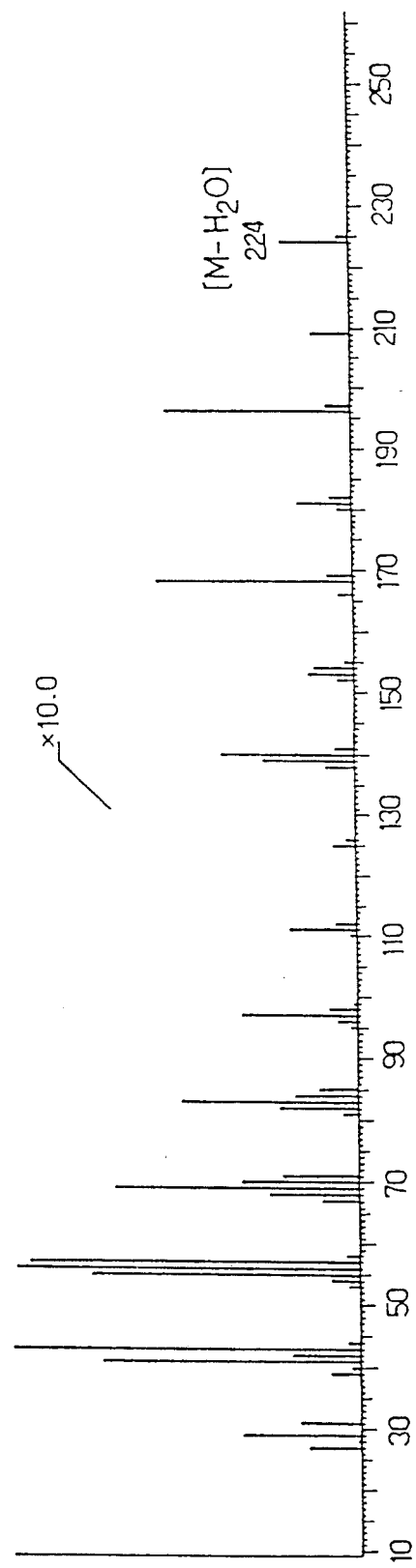
Figure 4:
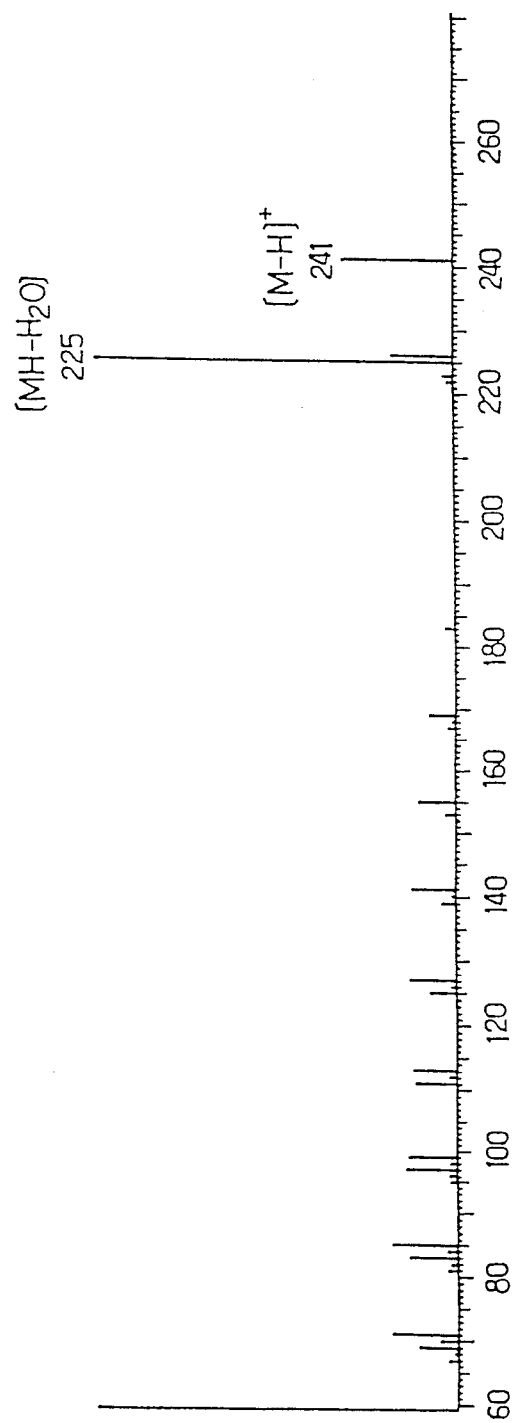
Figure 5:
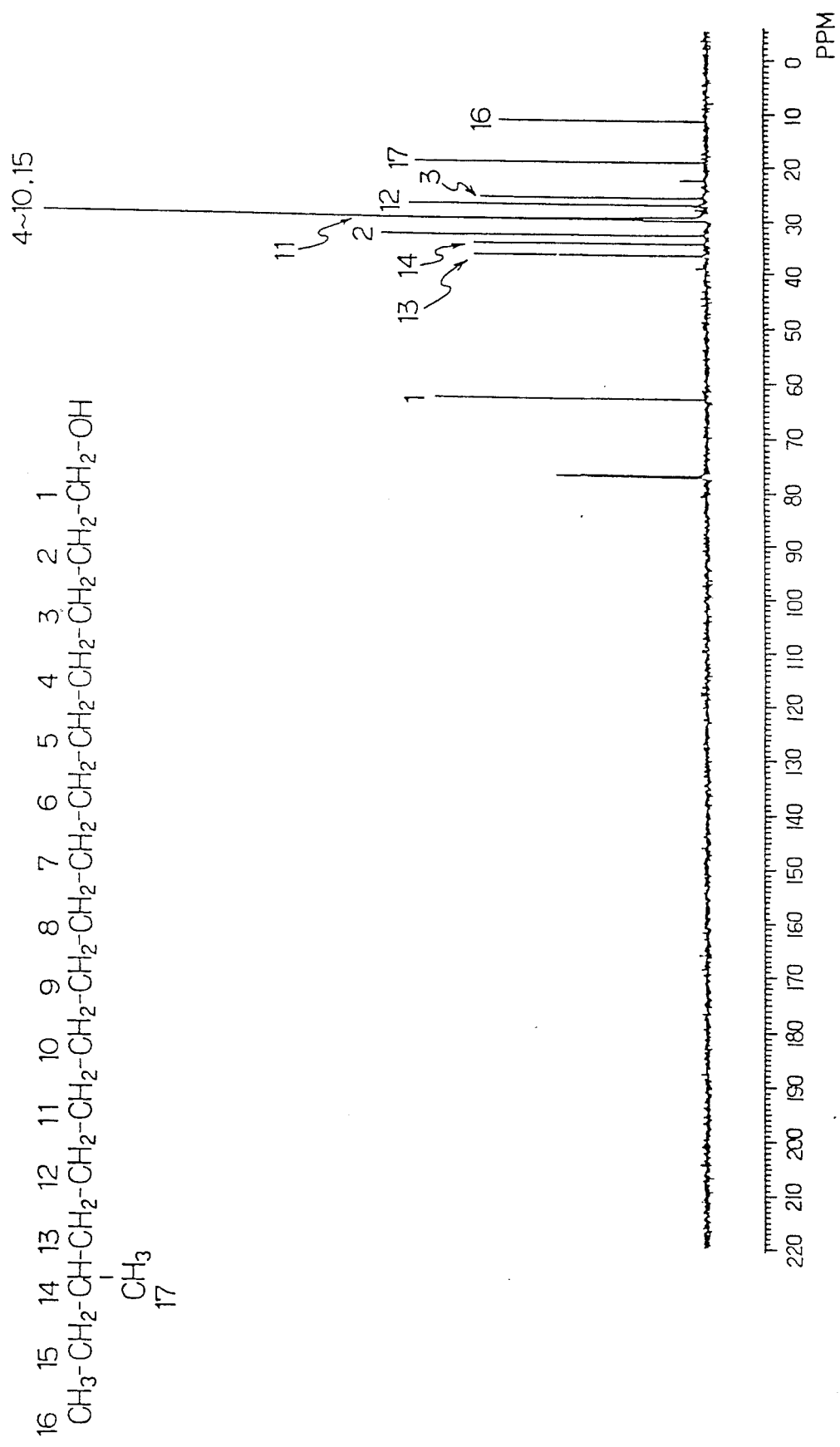
Figure 6:
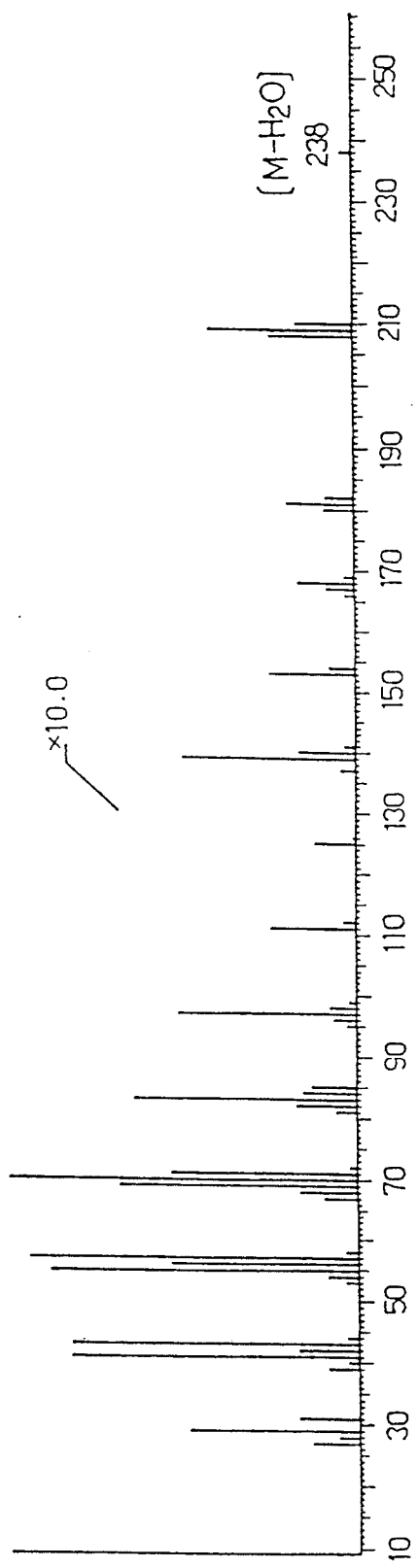
Figure 7:
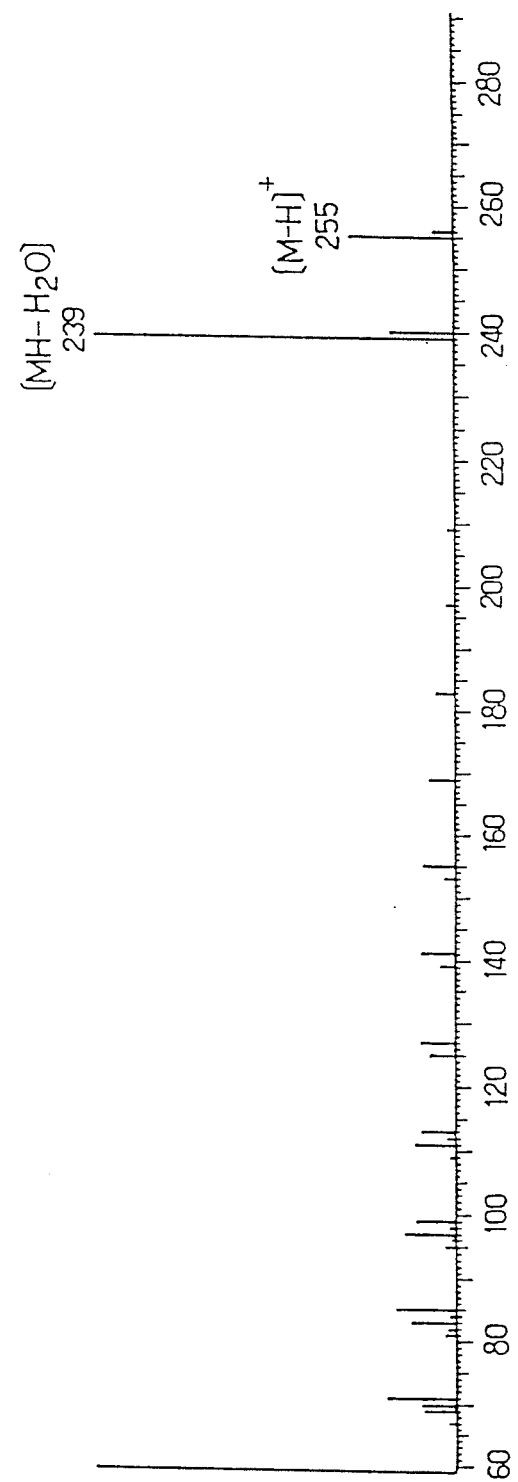

FIG. 2 shows a $^{13}C$-NMR spectrum (100.40 MHz, $CDCl_3$, $\delta$ ppm) of 14-methyl-1-pentadecanol, and FIG. 3 and FIG. 4 show GC-MS data thereof. FIG. 5 shows a $^{13}C$-NMR spectrum (100.40 MHz, $CDCl_3$, $\delta$ ppm) of 14-methyl-1-hexadecanol, and FIG. 6 and FIG. 7 show GC-MS data thereof. Data shown in FIG. 3 and FIG. 6 were obtained in mode EI with an ionizing voltage of 70 eV and with the temperature of the ion source of 250° C. Data shown in FIG. 4 and FIG. 7 were obtained in mode CI using isobutane as reacting gas, with an ionizing voltage of 200 eV and with the temperature of the ion source of 250° C.

The isomonools obtained above were tested for carcinostatic, carcinostasis-reinforcing activity.

TEST 1

5-week old ddY mice were intraperitoneally inoculated with $10^6$ Ehrlich's ascites carcinoma cells. Since 24 hours later, 50 mg/ml suspension of a test compound in 0.25% (% by weight. The definition is to be followed hereinafter) solution of Pluronic F68 in physiological saline was intraperitoneally injected to 10 animals/group at a dose of 10 mg/kg/day for 5 days.

The mean survival time after inoculation was 14.0 days for the group administered the carrier solution containing none of the test compounds. On the other hand, the mean survival time of the animal group administered the test compounds was 60 days or more for 14-methyl-1-pentadecanol, 57.5 days for 14-methyl-1-hexadecanol, and 60 days or more for their 1:1 mixture. The effects on prolonging the survival time were statistically significant.

TEST 2

6-week old $F_1$ mongrel mice of C57BL/6 and DBA/2 were inoculated under back skin with $10^6$ adenocarcinoma 755 cells. Since 24 hours later, 50 mg/ml suspension of a test compound in 0.25% HCO-60 solution in physiological saline was subcutaneously injected to 8 animals/group at a dose of 10 mg/kg/day for 5 days. The animals were sacrificed 10 days after the inoculation with adenocarcinoma 755 cells, and the tumor was excised.

The mean tumor weight (g) of the control group was 6.5. On the other hand, that was 1.6 and 2.3 for the group administered 16-methyl-1-heptadecanol and 16-methyl-1-octadecanol, respectively. The tumor growth suppressing effects were statistically significant.

TEST 3

14-methyl-1-pentadecanol and 18-methyl-1-nonadecanol were tested for tumor growth suppressing effects on three different tumor cell strains (Ehrlich's mouse ascites carcinoma cells, human lung carcinoma A549 cells and mouse neuroblastoma NAs-1 cells). As the results, the two isomonools were demonstrated to be effective on any of these three types of tumor cells.

These isomonools suppressed the colony formation rate of human lung A549 cells to $2.2 \times 10^{-3}$ and $4.1 \times 10^{-3}$, respectively, by 6-hour treatment at 10 $\mu M$.

These isomonools suppressed the growth of Ehrlich's ascites carcinoma cells to $4.5 \times 10^{-3}$ and $1.5 \times 10^{-2}$, respectively, by 5-day treatment at 10 $\mu M$.

The growth of mouse neuroblastoma NAs-1 cells was suppressed to $7.8 \times 10^{-3}$ and $6.5 \times 10^{-3}$, respectively.

TESTS 4 AND 5, AND COMPARING TEST 1

The cytocidal activity ($IC_{90}$) of bleomycin was evaluated when used alone or used in combination with 14-methyl-1-pentadecanol or 14-methyl-1-hexadecanol, using Ehrlich's mouse ascites carcinoma cells and human lung tumor A549 cells. The results are shown in Table 1.

As clearly shown from the results in Table 1, when the isomonools of the present invention is used in combination with a carcinostatic agent, the cytocidal effect is markedly increased in comparison with the case where the carcinostatic agent is used alone.

TEST 6 AND COMPARING TEST 2

The amount of bleomycin taken up into Ehrlich's ascites cells was determined as a function of time in the case where bleomycin (60 μg/ml) was used in combination with 14-methyl-1-pentadecanol (0.05 μM). The results are shown in Table 2.

As clearly shown from the result in Table 2, when the isomonool of the present invention is used in combination with a carcinostatic agent, the uptake of the carcinostatic agent into Ehrlich's cells is rapidly increased in comparison with the case where the carcinostatic agent is used alone.

TEST 7 AND COMPARING TESTS 3 AND 4

5-week old male C57BL/6 mice were intraperitoneally inoculated with $10^6$ Ehrlich's mouse ascites carcinoma cells. Since 24 hours later, a 50 μg/ml solution of bleomycin in 0.25% HCO-60 solution in physiological saline, and a suspension containing 50 μg/ml of bleomycin and 5 μg/ml of 14-methyl-1-pentadecanol were intraperitoneally injected at a dose of 10 mg/kg·day and 11 mg/kg·day, respectively, to each 8 animals/group for 5 days. The survival time of the injected mice was then followed. The results are shown in table 3.

As shown in Table 3, the mean survival time after inoculation was 33.3 days for the group (Comparing test 3) which was administered the bleomycin solution containing none of the carcinostasis-reinforcing agents of the present invention, whereas the mean survival time after inoculation was 54.3 days for the group (Test 7) which was administered the bleomycin solution containing one of the isomonools as a carcinostasis-reinforcing agent of the present invention.

Thus, it is demonstrated that the isomonools of the present invention are useful as carcinostasis-reinforcing agents.

TEST 8

6-week old female SD rats (n=90) were treated as follows using 14-methyl-1-pentadecanol as a carcinogenesis-preventing agent.

Unadministered group: n=30. MF powder feed (ORIENTAL KOBO K.K.) was given as a basic feed.

Administered group A: n=30. A test feed was given continually (for 7 days). The feed was prepared by admixing the said carcinogenesis-preventing agent (after emulsified in Pluronic F-68) with the above-mentioned basic feed in an amount of 50 mg/kg.

Administered group B: n=30. A test feed was given continually (for 7 days). The feed was prepared by admixing the said carcinogenesis-preventing agent (after emulsified in Pluronic F-68) with the above-mentioned basic feed in an amount of 250 mg/kg.

Among these groups, there were no significant differences in the amount of feed consumed.

After the aforementioned treatment, 5 mg/body of benzanthracene (DMBA: a carcinogenic compound) was administered by injecting subcutaneously in mammary gland 0.1 ml/body of a 50 mg/ml benzanthracene solution. Then, each of the aforementioned groups was given corresponding feed for 20 weeks.

Among these groups, there were no significant differences in the amount of feed consumed.

After the completion of the treatment, the rats were sacrificed and observed for the occurrence of mammary cancer. The results are shown in Table 4.

TEST 9

40 male Wistar rats (8-9-week old, body weight; 110 g) were given a drinking water containing 167 μg/ml of N-methyl-N'-nitro-N-nitrosoguanidine (MNNG: a carcinogenic compound) and a feed (dry pellets CE-2, produced by CLEA JAPAN) for 210 days.

On the 210th day, adenoma-like hyperplasia was observed in the stomach.

The rats were allotted to 5 groups and treated as follows since the 211th day.

Unadministered group: n=8.

Administered group A: n=8. The compound A of the present invention (See below. The definition is to be followed hereinafter) was administered orally in an amount of 250 mg/kg feed for 126 consecutive days.

Administered group B: n=8. The compound B of the present invention was administered orally in an amount of 250 mg/kg feed for 126 consecutive days.

Administered group C: n=8. The compound C of the present invention was administered orally in an amount of 250 mg/kg feed for 126 consecutive days.

Administered group D: n=8. The compound D of the present invention was administered orally in an amount of 250 mg/kg feed for 126 consecutive days.

A: 14-methyl-1-pentadecanol
B: 14-methyl-1-hexadecanol
C: 16-methyl-1-heptadecanol
D: 16-methyl-1-octadecanol.

On the 337th day, the surviving rats were sacrificed and the stomachs were (1) subjected to Borrmann's classification according to gross observation and (2) histologically observed (haematoxylin-eosin stain or ASAN stain), and then classified as follows. The results are shown in Table 5.

Grade O: No stomach carcinoma are observed.
Grade I: Stomach carcinoma within mucous membrane.
Grade II: Stomach carcinoma infiltrating beneath mucous membrane.
Grade III: Stomach carcinoma infiltrating into muscle layers or serous membrane.
Grade IV: Stomach carcinoma metastasizing to adjacent lymph nodes, duodenum or jejunum.

TEST 10

5 groups of 6-week old male F344 rats were givn 0.05% (by weight. The definition is to be followed hereinafter) aqueous solution of N-butyl-N-(4-hydroxybutyl)nitrosoamine (BBN: bladder carcinogenic compound), as an initiator, by water supplying bottles for 4 weeks. Then the animals were given 5% sodium erythorbate aqueous solution, as a promoter (carcinogenesis promoting compound), and a feed which was prepared by admixing one of the compounds A-D of the present invention (See below) with the MF powder feed produced by ORIENTAL KOBO K.K. in an amount of 250 mg/kg.

A: 14-methyl-1-heptadecanol
B: 14-methyl-1-hexadecanol
C: 16-methyl-1-heptadecanol
D: 18-methyl-1-nonadecanol.

Among the animal groups, there were no significant differences in the amount of feed consumed.

After these treatment is completed, the rats were sacrificed and observed for the occurrence of pathological changes in bladder mucous membrane. The results are shown in Table 6.

The carcinostatic, carcinostasis-reinforcing and carcinogenesis-preventing compositions of the present invention exhibit excellent effects, whereas the active ingredients thereof are obtained from organisms (higer animals) and, thus, may not cause severe side effects on organisms.

TABLE 1

| Test | Carcinostatic agent | Carcinostasis reinforcing agent (0.05 μM) | Cytocidal activity (IC90 (μg/ml)) Ehrlich's mouse ascites carcinoma cells | Human lung carcinoma A549 cells |
|---|---|---|---|---|
| 4 | bleomycin | iso-$C_{16}$—OH* | 4.0 | 28 |
| 5 | bleomycin | iso-$C_{17}$—OH*[2] | 6.0 | 24 |
| Comparing T.1 | bleomycin | — | 20 | 44 |

*[1] 14-methyl-1-pentadecanol
*[2] 14-methyl-1-hexadecanol

TABLE 2

| Test | Carcinostatic agent | Carcinostasis reinforcing agent | Bleomycin uptake with lapse of time (μg/mg Ehrlich's cell) Initial | 30 | 60 | 120 | 180 (min) |
|---|---|---|---|---|---|---|---|
| 6 | bleomycin | iso-$C_{16}$—OH*[1] | 0 | 0.13 | 0.26 | 0.39 | 0.55 |
| Comparing. 2 | bleomycin | — | 0 | 0.03 | 0.06 | 0.12 | 0.13 |

*[1] 14-methyl-1-pentadecanol

TABLE 3

| Test | Carcinostatic agent | Carcinostasis reinforcing agent | 0 | 14 | 15 | 16 | 17 | 18 | 19 | 20 | 23 | 33 | 41 | 45 | 52 | 57 | 60 |
|---|---|---|---|---|---|---|---|---|---|---|---|---|---|---|---|---|---|
| 7 | bleomycin | iso-$C_{16}$—OH*[1] | 8 | 8 | 8 | 8 | 8 | 8 | 8 | 8 | 8 | 8 | 8 | 6 | 4 | 4 | 4 |
| Comparing. 3 | bleomycin | — | 8 | 7 | 6 | 6 | 6 | 6 | 6 | 6 | 4 | 3 | 2 | 2 | 2 | 1 | 1 |
| Comparing. 4 | — | — | 8 | 8 | 6 | 5 | 4 | 3 | 1 | 0 | 0 | 0 | 0 | 0 | 0 | 0 | 0 |

Number of surviving mice with the lapse of time (day)

*[1] 14-methyl-1-pentadecanol

TABLE 4

| Group | Number of animals with mammary cancer/Number of tested animals |
|---|---|
| Administered group A | 8/30 |
| Administered group B | 4/30 |
| Unadministered group | 15/30 |

TABLE 5

| Group (animal No.) | | Cause of death | Survival time (day) | Borrmann's Classification | Histological classification |
|---|---|---|---|---|---|
| Administered group A | (1) | sacrificed | 337 | I | I |
| | (2) | " | " | 0 | 0 |
| | (3) | " | " | 0 | 0 |
| | (4) | " | " | 0 | 0 |
| | (5) | " | " | 0 | 0 |
| | (6) | " | " | I | I |
| | (7) | " | " | 0 | 0 |
| | (8) | " | " | 0 | 0 |
| Administered group B | (1) | " | " | I | I |
| | (2) | " | " | 0 | 0 |
| | (3) | " | " | 0 | 0 |
| | (4) | " | " | 0 | 0 |
| | (5) | " | " | 0 | 0 |
| | (6) | " | " | 0 | 0 |
| | (7) | " | " | I | I |
| | (8) | " | " | I | II |
| Administered group C | (1) | dead in cage | 305 | II | III |
| | (2) | sacrificed | 337 | 0 | 0 |
| | (3) | " | " | I | I-II |
| | (4) | " | " | 0 | 0 |
| | (5) | " | " | 0 | 0 |
| | (6) | " | " | 0 | 0 |
| | (7) | " | " | 0 | 0 |
| | (8) | " | " | II | II |
| Administered group D | (1) | dead in cage | 301 | III | III |
| | (2) | " | 312 | III | III |
| | (3) | sacrificed | 337 | I | I |
| | (4) | " | " | 0 | 0 |
| | (5) | " | " | 0 | 0 |
| | (6) | " | " | I | I-II |
| | (7) | " | " | I | I-II |
| | (8) | " | " | I | II |
| Unadministered group | (1) | dead in cage | 238 | IV | IV |
| | (2) | " | 270 | IV | IV |
| | (3) | " | 270 | IV | IV |
| | (4) | " | 273 | IV | IV |
| | (5) | " | 280 | IV | IV |

TABLE 5-continued

| Group (animal No.) | Cause of death | Survival time (day) | Borrmann's Classification | Histological classification |
| --- | --- | --- | --- | --- |
| (6) | " | 281 | IV | IV |
| (7) | " | 285 | IV | IV |
| (8) | sacrificed | 337 | III | III |

TABLE 6

| Group | | Number of observed animals | Number of animals with pathological changes in bladder mucous membrane (incidence, %) | | |
| --- | --- | --- | --- | --- | --- |
| | | | Papillary or tuberous hyperplasia | Papilloma | Cancer |
| Administered group | A | 28 | 0 (0) | 0 (0) | 0 (0) |
| | B | 28 | 0 (0) | 0 (0) | 0 (0) |
| | C | 28 | 1 (4) | 0 (0) | 0 (0) |
| | D | 28 | 2 (7) | 0 (0) | 0 (0) |
| Unadministered group | | 27 | 27 (100) | 20 (74) | 19 (70) |

What is claimed is:

1. A method of treatment for suppressing the growth of a tumor in an animal having a tumor which is susceptible to such treatment which consists essentially of administering orally or parenterally an anti-tumor effective amount of an isomonool $$CH_3CH(CH_2)_nCH_2OH \qquad (I)$$
$$|$$
$$CH_3$$

selected from a group consisting of 14-methyl-1-pentadecanol, 14-methyl-1-hexadecanol, 16-methyl-1-heptadecanol, 16-methyl-1-octadecanol and 18-methyl-1-nonadecanol.

2. The method of claim 1 wherein the isomonool is 14-methyl-1-pentadecanol.

3. The method of claim 1 wherein the isomonool is 14-methyl-1-hexadecanol.

4. The method of claim 1, wherein the isomonool is administered concurrently with a known anti-cancer chemotherapeutic agent.

5. The method of claim 4, wherein the known anti-cancer agent is bleomycin.

6. In a method of treating an animal with a carcinoma with a carcinostatic agent, the improvement which consists essentially of orally or parenterally administering to an animal administered the carcinostatic agent in combination with an amount effective to enhance the carcinostatic activity thereof of an isomonool selected from a group consisting of 14-methyl-1-pentadecanol, 14-methyl-1-hexadecanol, 16-methyl-1-heptadecanol, 16-methyl-1-octadecanol and 18-methyl-1-nonadecanol.

7. The method of claim 6 wherein the isomonool is 14-methyl-1-pentadecanol.

8. The method of claim 6 wherein the isomonool is 14-methyl-1-hexadecanol.

* * * * *